(12) United States Patent
Warlick et al.

(10) Patent No.: US 8,529,451 B2
(45) Date of Patent: Sep. 10, 2013

(54) SHOCK WAVE COUPLING ADAPTER AND METHOD OF USE

(75) Inventors: John Warlick, Woodstock, GA (US); Michael F Rozmajzl, Woodstock, GA (US)

(73) Assignee: General Patent, LLC, Marietta, GA (US)

( * ) Notice: Subject to any disclaimer, the term of this patent is extended or adjusted under 35 U.S.C. 154(b) by 708 days.

(21) Appl. No.: 12/236,104

(22) Filed: Sep. 23, 2008

(65) Prior Publication Data

US 2009/0088670 A1   Apr. 2, 2009

Related U.S. Application Data

(60) Provisional application No. 60/976,559, filed on Oct. 1, 2007.

(51) Int. Cl.
*A61B 8/00* (2006.01)

(52) U.S. Cl.
USPC .............. 600/441; 600/407; 600/437; 601/2; 601/4

(58) Field of Classification Search
USPC .......................... 600/437, 407, 441; 601/2, 4
See application file for complete search history.

(56) References Cited

U.S. PATENT DOCUMENTS

| | | | |
|---|---|---|---|
| 4,539,989 A | 9/1985 | Forssmann et al. | |
| 4,807,627 A | 2/1989 | Eisenmenger | |
| 5,119,801 A | 6/1992 | Eizenhoefer et al. | |
| 5,174,280 A | 12/1992 | Gruenwald et al. | |
| 5,222,484 A | 6/1993 | Krauss et al. | |
| 5,419,335 A | 5/1995 | Hartmann et al. | |
| 7,326,201 B2 * | 2/2008 | Fjield et al. | 606/27 |
| 7,507,213 B2 * | 3/2009 | Schultheiss et al. | 601/2 |
| 2005/0038362 A1 * | 2/2005 | Schultheiss | 601/4 |
| 2006/0100550 A1 | 5/2006 | Schultheiss et al. | |
| 2007/0066897 A1 * | 3/2007 | Sekins et al. | 600/437 |

FOREIGN PATENT DOCUMENTS

EP   1445758   8/2004

* cited by examiner

*Primary Examiner* — Joel Lamprecht
(74) *Attorney, Agent, or Firm* — David L. King

(57) ABSTRACT

A shock wave adapter for use with a focused shock wave applicator has a flexible, rigid or semi-rigid membrane or housing adapted to be filled with a fluid. The membrane or housing is devoid of any air or gases and when filled forms a spacer volume for passing acoustic shock waves at low impedance. The wave pattern of the shock wave applicator enters the membrane or housing as a converging wave form to a focus inside the membrane or housing and exits through the membrane or housing in a diverging wave form into the patient to be treated. The spacer adapter may further include a gas filled shield around the perimeter of the fluid filled membrane or housing to block transmissions of acoustic shock waves.

17 Claims, 4 Drawing Sheets

SHOCK WAVE COUPLING ADAPTER AND METHOD OF USE

RELATED APPLICATIONS

This application claims priority to U.S. divisional application 60/976,559 filed on Oct. 1, 2007 entitled "Shock Wave Coupling Adapter and Method of Use".

TECHNICAL FIELD

The present invention relates to a device for use with acoustic shock wave generation sources, more particularly to an adapter for use with acoustic shock wave applicator heads and its method of use.

BACKGROUND OF THE INVENTION

Electro-hydraulic shock wave systems have been used to disintegrate kidney and urethral stones by applying focused shock waves to the stones. A few hundred up to a few thousand shock waves may be required to break a stone within a mammal into small pieces of 3 to 4 mm diameter which would be able to pass over a period of several weeks through the urethra and the bladder out of the patient's body.

Devices using electro-hydraulic (U.S. Pat. No. 4,539,989), piezoceramic (U.S. Pat. No. 5,119,801) or electro-magnetic (U.S. Pat. No. 5,174,280) shock wave or pressure pulse generating elements have been described and are known in the art.

Known devices generally make use of more or less strong focused shock waves which are focused by ellipsoidal reflectors and electro-hydraulic devices as in U.S. Pat. No. 4,539,989 or by parabolic reflectors in devices using electro-magnetic sources which are emitting waves from a cylindrical surface as in U.S. Pat. No. 5,174,280. Other electro-magnetic sources may make use of acoustic lenses of different shapes, for example concave or convex depending on the sound velocity and density of the lens material used as described in U.S. Pat. No. 5,419,335 and EP 1 445 758 A2. Piezoelectric sources often use spherical surfaces to emit acoustic shock waves which are self focused to the center of the sphere as described in U.S. Pat. No. 5,222,484. The same type of focusing has been used in spherical electro-magnetic devices as described in U.S. Pat. No. 4,807,627.

As can readily be appreciated a large investment is made into these shock wave generating pieces of equipment. The primary purpose of the equipment is to generate relatively high intensity acoustic shock waves that would converge to a focal point or focal region to perform a specific task within a patient, such as the breaking up of concrements.

New applications have been discovered wherein it appears that much lower and relatively unfocused or non-focused shock waves are required to treat a certain tissue, this is particularly true of soft tissue such as skin muscle or any organ underlying the skeletal surface. As a result the effects of a focused shock wave can create a damaging effect creating localized hemorrhaging and cellular disruption in the treated area. To avoid this it has been proposed in several patent applications that the use of lower energy, unfocused shock waves should be attempted. One such publication US 2006/0100550 entitled "Pressure Pulse/Shock Wave Therapy Methods and An Apparatus For Conducting the Therapeutic Methods" was published on May 11, 2006. In this publication it was taught that the use of acoustic shock waves having a focal point could be effectively used if the focal point was shifted such that the targeted tissue was either inward of the focal volume. In other words between the source emitted from the lens of the acoustic shock wave head and prior to the convergence to a focal point such that the focal point lies outside the treated tissue, preferably outside the patient's body. In this way the acoustic shock waves would be presented in a converging pattern, but would impinge the treated tissue prior to achieving a high energy focused acoustic shock wave. Additionally it was proposed that conventional acoustic shock wave generators could be used wherein the treated tissue was positioned outward of the focal point such that the acoustic shock wave would generate a focal point inside the lens or inside of the applicator head and that the generated wave or tissue would then come out in a divergent pattern as such the treated tissue would be exposed to a diverging acoustic shock wave head of lower energy than at the focal region.

In this application it was suggested that modification to the focal point within the equipment could be accomplished by generating adjustments to the lens and or the ellipsoid or by changing different physical parameters of the equipment to achieve the desired results.

In practice this becomes much more difficult to achieve in that the equipment currently in the market is not readily adapted to these types of adjustments, normally the ellipsoid was designed such that the treatment area would be a few mm inward from the skin of the patient such that the focal point could be precisely set within a given limited per-set range. In order to adjust outside this range with pre-existing equipment a tremendous amount of manipulation must occur and precise settings could not be adequately determined. It has therefore been proposed that special unfocused shock wave generating heads be developed. In the interim, however, a large amount of equipment currently in the hands of medical practitioners is unsuitable for this purpose. It has been determined that an adapter that could permit the targeted tissue to avoid any high focused energy from the acoustic shock waves would be desirable. As a result of this appreciation and understanding of the limitations of the equipment currently in the marketplace, the inventors of the present invention as described in this application have come up with a novel and simple way of permitting the use of conventional focused shock wave generators in a way that will achieve treatment of unfocused shock waves.

SUMMARY OF THE INVENTION

A shock wave adapter for use with a focused shock wave applicator has a flexible, rigid or semi-rigid membrane or housing adapted to be filled with a fluid. The membrane or housing is devoid of any air or gases and when filled forms a spacer volume for passing acoustic shock waves at low impedance. The wave pattern of the shock wave applicator enters the membrane or housing as a converging wave form to a focus inside the membrane or housing and exits through the membrane or housing in a diverging wave form into the patient to be treated. The membrane or housing preferably is made of a flexible synthetic material. The material can be latex, polyurethane, silicon, polyethylene or any other flexible thermoplastic material suitable for transmission of acoustic shock waves. Alternatively, the housing may be semi-rigid or rigid made of suitable plastic or other material with good transmission properties for acoustic shock waves. The membrane or housing further may comprise a fill valve for adding fluid. The membrane or housing is preferably pre-filled with a degassed water based solution either at the time of manufacture or at the time of use. The spacer adapter may further include a gas filled shield around the perimeter of the fluid filled membrane or housing to block transmissions of acoustic shock waves. The membrane or housing can be packaged in sterility barrier packaging and sterilized prior to use whether in the filled or un-filled condition. The membrane or housing can be designed to be reusable in some applications or alternatively can be made as a disposable device for one time use only. The shock wave adapter is preferably used in the following way wherein a method of treating tissue with a focused shock wave generating source has the steps of establishing the distance from the shock wave generating sources lens to a theoretical focal point; positioning a fluid membrane or housing between the tissue and the lens wherein the focal point is located inside the membrane or housing; and thereafter activating the focused shock wave generating source having the focal point impinge inside the membrane or housing and exit as a divergent wave pattern into the tissue to be treated. In this fashion the focus occurs entirely inside the spacer volume created by the membrane or housing and thereafter the tissue of the patient is only impinged with a diverging wave pattern preferably of lower energy such as to avoid any localized hemorrhaging or pain sensation as is commonly achieved with the alternative focused shock wave treatments.

DEFINITIONS

A "curved emitter" is an emitter having a curved reflecting (or focusing) or emitting surface and includes, but is not limited to, emitters having ellipsoidal, parabolic, quasi parabolic (general paraboloid) or spherical reflector/reflecting or emitting elements. Curved emitters having a curved reflecting or focusing element generally produce waves having focused wave fronts, while curved emitters having a curved emitting surfaces generally produce wave having divergent wave fronts.

"Divergent waves" in the context of the present invention are all waves which are not focused and are not plane or nearly plane. Divergent waves also include waves which only seem to have a focus or source from which the waves are transmitted. The wave fronts of divergent waves have divergent characteristics. Divergent waves can be created in many different ways, for example: A focused wave will become divergent once it has passed through the focal point. Spherical waves are also included in this definition of divergent waves and have wave fronts with divergent characteristics.

"Extracorporeal" occurring or based outside the living body or plant structure.

A "generalized paraboloid" according to the present invention is also a three-dimensional bowl. In two dimensions (in Cartesian coordinates, x and y) the formula $y^n=2px$ [with n being $\neq 2$, but being greater than about 1,2 and smaller than 2, or greater than 2 but smaller than about 2,8]. In a generalized paraboloid, the characteristics of the wave fronts created by electrodes located within the generalized paraboloid may be corrected by the selection of (p (−z,+z)), with z being a measure for the burn down of an electrode, and n, so that phenomena including, but not limited to, burn down of the tip of an electrode (−z,+z) and/or disturbances caused by diffraction at the aperture of the paraboloid are compensated for.

A "paraboloid" according to the present invention is a three-dimensional reflecting bowl. In two dimensions (in Cartesian coordinates, x and y) the formula $y^2=2px$, wherein p/2 is the distance of the focal point of the paraboloid from its apex, defines the paraboloid. Rotation of the two-dimensional figure defined by this formula around its longitudinal axis generates a de facto paraboloid.

"Plane waves" are sometimes also called flat or even waves. Their wave fronts have plane characteristics (also called even or parallel characteristics). The amplitude in a wave front is constant and the "curvature" is flat (that is why these waves are sometimes called flat waves). Plane waves do not have a focus to which their fronts move (focused) or from which the fronts are emitted (divergent). "Nearly plane waves" also do not have a focus to which their fronts move (focused) or from which the fronts are emitted (divergent). The amplitude of their wave fronts (having "nearly plane" characteristics) is approximating the constancy of plain waves. "Nearly plane" waves can be emitted by generators having pressure pulse/shock wave generating elements with flat emitters or curved emitters. Curved emitters may comprise a generalized paraboloid that allows waves having nearly plane characteristics to be emitted.

A "pressure pulse" according to the present invention is an acoustic pulse which includes several cycles of positive and negative pressure. The amplitude of the positive part of such a cycle should be above about 0.1 MPa and its time duration is from below a microsecond to about a second. Rise times of the positive part of the first pressure cycle may be in the range of nano-seconds (ns) up to some milli-seconds (ms). Very fast pressure pulses are called shock waves. Shock waves used in medical applications do have amplitudes above 0.1 MPa and rise times of the amplitude are below 100 ns. The duration of a shock wave is typically below 1-3 micro-seconds (µs) for the positive part of a cycle and typically above some micro-seconds for the negative part of a cycle.

"Waves/wave fronts" described as being "focused" or "having focusing characteristics" means in the context of the present invention that the respective waves or wave fronts are traveling and increase their amplitude in direction of the focal point. Per definition the energy of the wave will be at a maximum in the focal point or, if there is a focal shift in this point, the energy is at a maximum near the geometrical focal point. Both the maximum energy and the maximal pressure amplitude may be used to define the focal point.

BRIEF DESCRIPTION OF THE DRAWINGS

The invention will be described by way of example and with reference to the accompanying drawings in which.

DETAILED DESCRIPTION OF THE INVENTION

Figure 1:
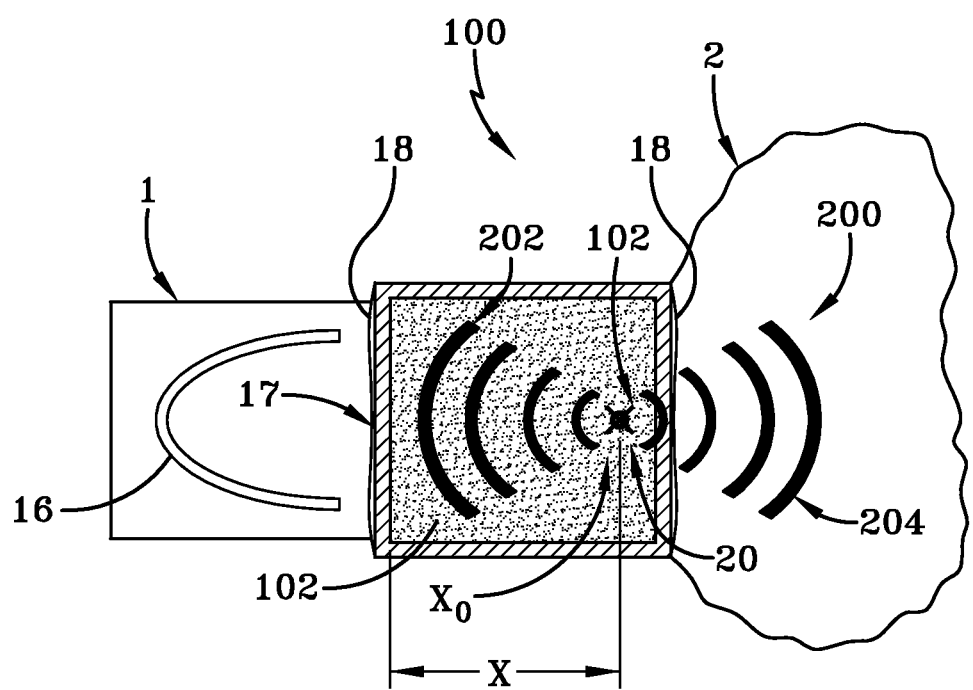
FIG. 1 is a simplified depiction of a pressure pulse/shock wave (PP/SW) generator applicator head and lens with focusing wave characteristics using the spacer adapter according to the present invention between the applicator lens and the treated tissue.
Figure 2:
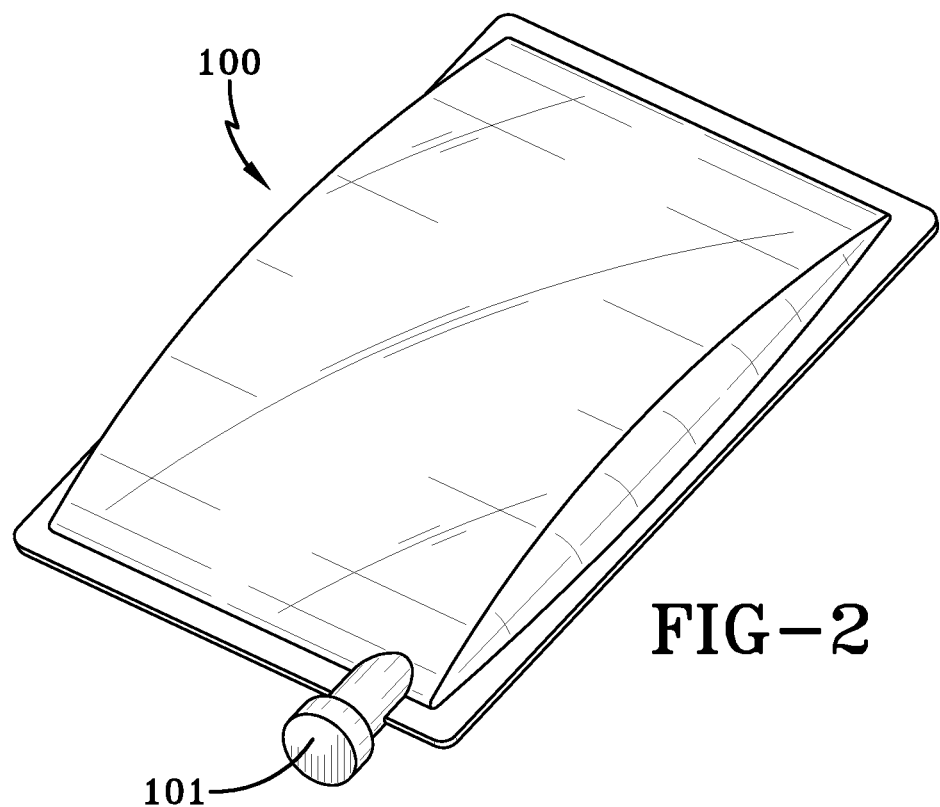
FIG. 2 is a perspective view of an exemplary flexible membrane according to the present invention.

With reference to FIG. 1, a shock wave applicator head 1 is shown having an ellipsoidal reflector 16 with a lens 17. The ellipsoid reflector 16 generates a focal focused shock wave 200. The focus 20 being at a distance from the lens 17 as illustrated at location $X_o$. Positioned between the lens and the patient's tissue 2 to be treated is a membrane or housing 100 filled with fluid 102. The membrane 100 as illustrated is preferably made of a plastic or synthetic material or latex material in such a fashion that it is reasonable conformable to the surface of the patient while at the same time providing a spacer volume of preferably degassed fluid 102 contained inside the membrane 100. In a preferred embodiment shown in FIG. 2, by having the membrane 100 of a sufficient flexibility, the thickness or space between the lens 17 and tissue 2 can be varied by the amount of fluid filled through the fill port or valve 101 or by providing membranes 100 in the form of bag like structures of different sizes and shapes the physician can insure that the focal point 20 transmitted from the shock wave applicator head 1 will impinge into the spacer volume created by the fluid 102 filled membrane 100. Additionally, by inserting a syringe in the fill port 101 any entrapped air can be evacuated ensuring the spacer has a complete fluid path free of any entrapped air. As the shock waves 200 are generated leaving the applicator head 1 the wave pattern created is a converging wave pattern 202 as illustrated. Once the wave pattern 200 converges to a theoretical or actual focal point 20 the wave pattern 204 continues as a diverging wave pattern 204 as further illustrated. By positioning the membrane between the lens 17 and the patient 2, the wave pattern that impinges the tissue 2 to be treated will be a diverging wave pattern 204 generally of decreasing intensity or energy. This has been found to be quite beneficial in the treatment of soft tissue 2 and other treatments wherein the generation of acoustic waves 200 creates a beneficial stimulating cellular response in the treatment areas, however, it is the avoidance of a focused transmission 20 within the tissue 2 that permits the elimination of any sensation of pain or localized hemorrhaging. These treatments can be done with no or minimal cavitation bubbles being generated within the treated tissue. This has the advantage of minimizing any cellular damage generated by the transmission of the acoustic shock waves into the treated tissue. New technology has shown that the use of lower amplitudes and lower energy shock wave transmission into the treated tissue can have a benefit of avoiding the detrimental effects of localized hemorrhaging and pain sensation which is common with the use of focused shock waves 200. The added benefit of the present invention is that it can convert any conventional focused shock wave applicator 1 into a system capable of providing these diverging wave patterns 204 wherein the focus point or theoretical focal volume 20 of transmission is absorbed within the spacer volume created by the membrane housing 100.

Figure 3:
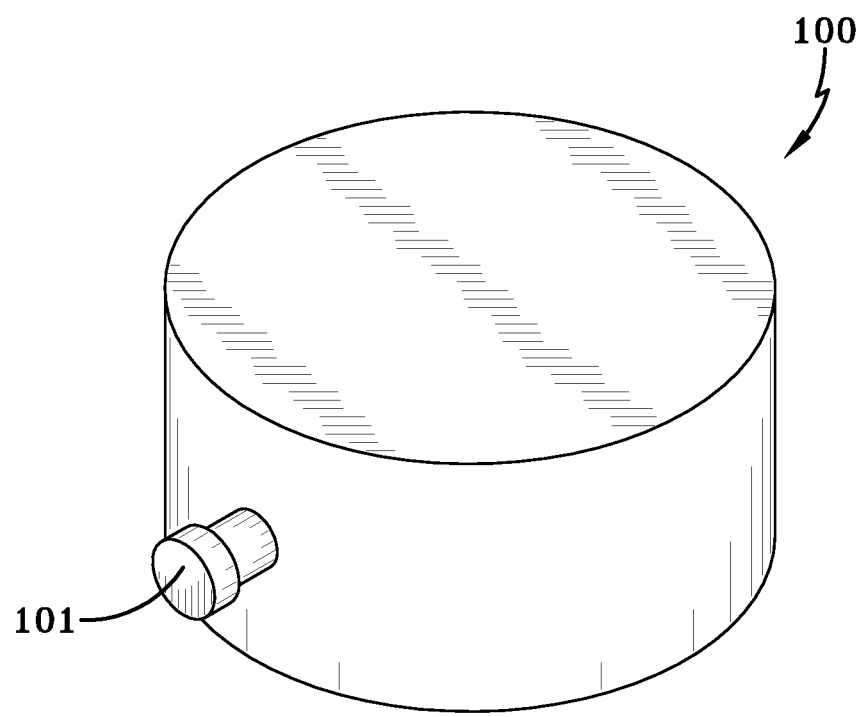
FIG. 3 is a perspective view of a semi-rigid or rigid housing according to the present invention.

In an alternative embodiment, shown in FIG. 3 the shock wave adapter 100 can be provided using a rigid membrane or housing 100 adapted to be filled with a fluid. The rigid membrane or housing 100 when filled with fluid is devoid of any air or gases. While working similar to the flexible membrane shown in FIG. 2, this spacer adapter 100 acts as a spacer for particular lenses 17 and shock wave heads 1 and therefore may be required to be sized for each application. In other words the thickness of the rigid membrane or housing 100 cannot be adjusted by the amount of fluid 102 added, but in fact is relatively fixed. However, this is perfectly acceptable in cases for a given device wherein the focus point 20 is generally predetermined within a certain range such that the rigid membrane or housing 100 can be applied as a spacer between a lens 17 of the shock wave head and the patient 2 to be treated in a similar fashion. In each application as described above the membrane or housing 100 whether rigid or flexible can be coated with an oil or acoustic gel layer 18 as shown in figure one which enhances the transmission between the spacer adapter 100 and the lens 17 and the spacer adapter 100 and the tissue 2. This is extremely important in that the transmission loss from the acoustic wave pattern 204 impinging on the tissue 2 must be kept to an absolute minimum. This is achieved primarily by insuring that there are no air or gas voids in the spacer adapter 100 or anywhere in between the spacer adapter 100 and the tissue 2 and the spacer adapter 100 and the lens 17 and further to insure that these devices are coupled in a very acoustically friendly fashion, preferably by layers 18 such that the transmission is done with virtually no loss of the acoustic energy.

Figure 4:
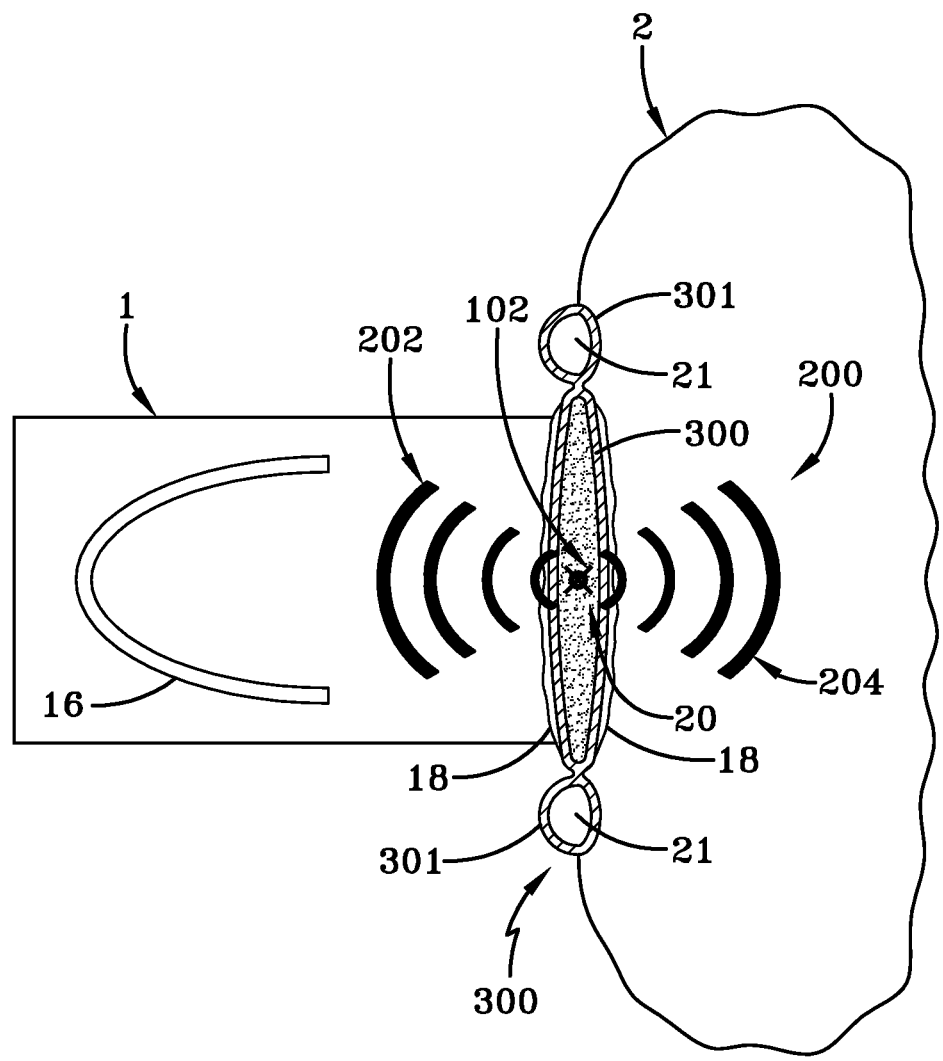
FIG. 4 is an alternative embodiment showing a simplified depiction of a pressure pulse/shock wave (PP/SW) generator applicator head and lens with focusing wave characteristics using the spacer adapter according to the present invention between the applicator lens and the treated tissue with a perimeter gas filled shield.
Figure 5:
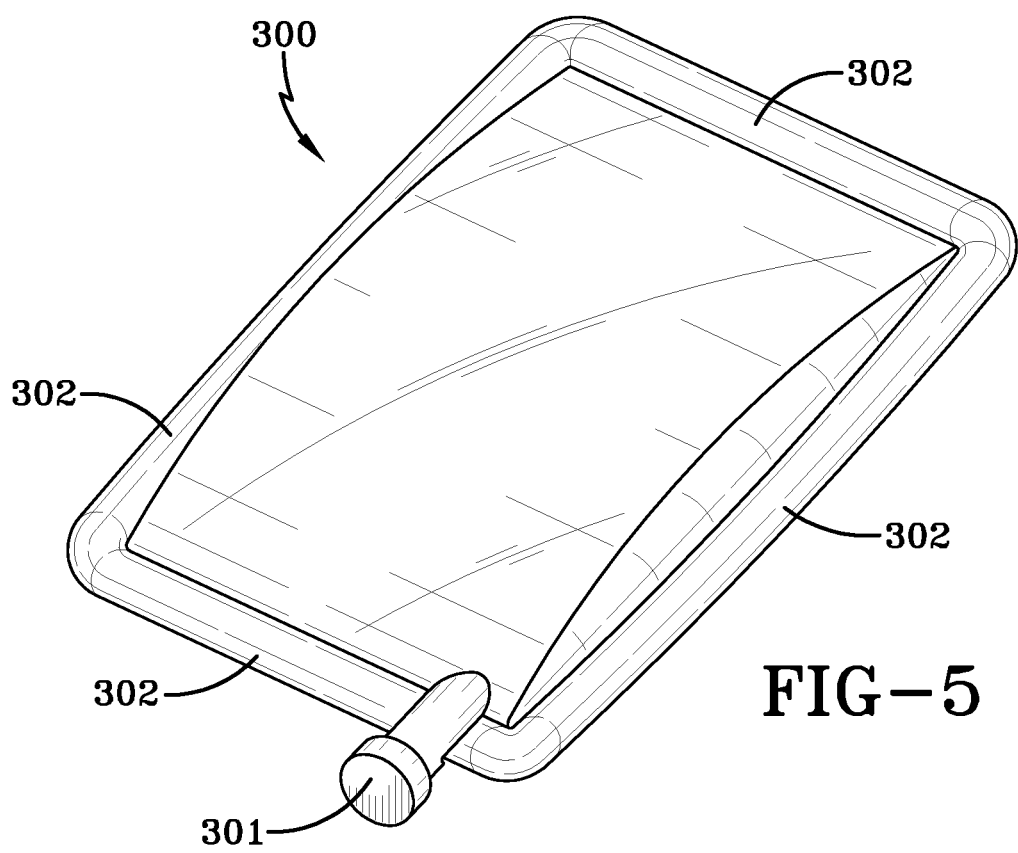
FIG. 5 is the alternative embodiment spacer adapter with a perimeter gas filled shield.

With reference to FIGS. 4 and 5 an alternative embodiment of the spacer adapter is shown. This spacer adapter 300 further includes a gas filled membrane encircling the perimeter of the spacer adapter in such a fashion that the fluid filled portion of the membrane was completely surrounded by an air or gas filled perimeter. This gas filled member 302 is preferably filled with air or nitrogen 21. During the treatment, a patient's tissue has the shock waves entering to the spacer adapter the shock waves converge to a focal point then diverge as they exit the focal point and enter the tissue in a diverging pattern as earlier discussed. In certain situations, different types of reflectors and movement of the spacer adapter could result in the shock waves impinging areas of the tissue that preferably should be isolated from any transmission of shock waves. In order to achieve this, the spacer adapter of the alternative embodiment 300 should be placed over the tissue 2 in such a way that the fluid filled portion is directly over the portion of the tissue 2 that the shock waves are to be transmitted to. As the shock wave head is moved from left to right or forward and aft relative to the spacer adapter 300 the emitted shock wave patterns may have portions of the shock waves trying to transmit around the perimeter of the spacer adapter 300. In such a situation, these shock waves 200 will impinge through the air filled member 302 and as soon as they do, the shock waves will dissipate. Shock waves do not transmit in gaseous fluids such as air and nitrogen, as a result the shock waves will self destruct in the gas filled shield 302. This shielding 302 is quite beneficial in that it prevents any area of sensitivity within the patient from being directly impinged with the shock waves and helps provide a perimeter protection for the patient preventing any acoustic shock waves from hitting any sensitive tissues such as lungs or other tissues that should be protected from any direct impingement of an acoustic shock wave. While in the preferred embodiment the use of the spacer adapter 300 is such that shock waves 200 of typically focused energy can be defocused by having the focal point positioned inside the fluid filled membrane 100 or 300 and come out with a diverging pattern absent a high energy peak as illustrated in FIGS. 1 and 4. This enables the tissue 2 to be treated without the sensation of localized hemorrhaging as was commonly practiced in earlier focused shock wave devices.

It will be appreciated that the apparatuses and processes of the present invention can have a variety of embodiments, only a few of which are disclosed herein. It will be apparent to the artisan that other embodiments exist and do not depart from the spirit of the invention. Thus, the described embodiments are illustrative and should not be construed as restrictive.

We claim:

1. A spacer for positioning between a patient and the lens of a focused shock wave applicator, the spacer comprises;
   a membrane being in the form of a bag-like structure or housing adapted to be filled with a fluid, the membrane or housing being devoid of any air or gasses, and when filled forms a spacer volume for passing acoustic shock waves at low impedance, wherein the space between the lens and the tissue is varied by the amount of fluid in the membrane and the wave pattern passing from the lens of the shock wave applicator enters through an oil or gel coated layer on the bag-like structure or housing and the lens as converging to a focus inside the membrane and exits through the opposite side of the membrane through an oil or gel coated layer on the bag like structure or housing coupled to the tissue in a diverging wave form into the tissue to be treated, the membrane being a spacer positioned separate from but adjacent to the shock wave applicator between a lens of the shock wave applicator and the patient.

2. The spacer of claim 1 wherein the membrane is a bag made of a synthetic material.

3. The spacer of claim 2 wherein the membrane is made of latex polyurethane, silicon, polyethylene or a flexible thermoplastic material.

4. The spacer of claim 2 wherein the membrane further comprises a fluid valve for adding fluid.

5. The spacer of claim 2 wherein the membrane is pre-filled with a degased water based solution.

6. The spacer of claim 2 wherein the membrane is packaged in a sterility barrier packaging and sterilized prior to use.

7. The spacer of claim 2 wherein the membrane is reusable.

8. The spacer of claim 2 wherein the membrane is disposable.

9. A spacer for positioning between a patient and the lens of a focused shock wave applicator, the spacer comprises;
   a membrane being in the form of a housing adapted to be filled with a fluid, the housing being devoid of any air or gasses, and when filled forms a spacer volume for passing acoustic shock waves at low impedance, wherein the space between the lens and the tissue is fixed by the size of the membrane and the wave pattern passing from the lens of the shock wave applicator enters through an oil or gel coated layer on the housing and the lens as converging to a focus inside the membrane and exits through the opposite side of the membrane through an oil or gel coated layer on the housing coupled to the tissue in a diverging wave form into the tissue to be treated, the membrane being a spacer positioned separate from but adjacent to the shock wave applicator between a lens of the shock wave applicator and the patient, wherein the housing is made of a thermoplastic material of low acoustic impedance.

10. The spacer of claim 9 wherein the housing is made of acrylic, polystyrene or polyethylene.

11. The spacer of claim 9 wherein the housing further comprises a fluid valve for adding fluid.

12. The spacer of claim 9 wherein the housing is pre-filled with a degased water based solution.

13. The spacer claim 9 wherein the housing is packaged in a sterility barrier packaging and sterilized prior to use.

14. The spacer claim 9 wherein the housing is reusable.

15. The spacer claim 9 wherein the housing is disposable.

16. The spacer of claim 1 further comprises:
   a gas filled shield located around the perimeter of the fluid filled membrane bag-like structure or housing.

17. A method of treating tissue with a focused shock wave generating source comprising:
   establishing a distance from a shock wave lens to a theoretical focal point;
   coating a fluid filled spacer with an oil or acoustic gel layer at locations between the lens and the spacer and similarly coating the fluid filled spacer a second location between the spacer and tissue to acoustically couple the two locations by placing the spacer between the lens and the tissue of the patient;
   adjusting the space between the lens and the tissue by the amount of fluid in the spacer;
   positioning the spacer between the tissue and the lens wherein the focal point when emitted is located inside the spacer; and
   activating the focused shock wave generating source having the focal point impinge inside the spacer and exit as a divergent wave pattern into the tissue to be treated.

* * * * *